United States Patent

Brayer et al.

Patent Number: 5,064,861
Date of Patent: Nov. 12, 1991

[54] ACYLATED AMINE COMPOUNDS WHICH ARE USEFUL FUNGICIGAL AGENTS

[75] Inventors: Jean-Louis Brayer, Nanteuil le Haudoin; Laurent Taliani, Pavillons Sous Bois; Jean Tessier, Vincennes, all of France

[73] Assignee: Roussel Uclaf, Paris, France

[21] Appl. No.: 454,685

[22] Filed: Dec. 21, 1989

[30] Foreign Application Priority Data

Dec. 22, 1988 [FR]  France ................. 88 16994

[51] Int. Cl.$^5$ ................. A01N 37/20; C07C 103/82; C07C 129/12
[52] U.S. Cl. ................. 514/617; 514/621; 514/457; 564/162; 564/169; 564/175; 564/183; 549/399
[58] Field of Search ............. 564/175, 162, 169, 183; 514/617, 621, 457; 549/399

[56] References Cited

U.S. PATENT DOCUMENTS 3,348,998 10/1967 Spencer ....................... 564/175
3,448,196 6/1969 Rumpf et al. ................ 564/175

OTHER PUBLICATIONS

Chemical Abstracts, vol. 86, No. 15, Abstract 86:106546y, p. 508, Apr. 11, 1977.
Chemical Abstracts, vol. 69, No. 7, Abstract 69:27754k, pp. 2600–2601, Aug. 12, 1968.

*Primary Examiner*—C. Warren Ivy
*Assistant Examiner*—Zinna Nottingham-Davis
*Attorney, Agent, or Firm*—Bierman and Muserlian

[57] ABSTRACT

A compound selected from the group consisting of a compound of the formula

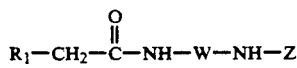

wherein $R_1$ is selected from the group consisting of Ar-O- and aryl, polyaryl and condensed polyaryl unsubstituted or substituted and heterocycle unsubstituted or substituted, Ar is aryl of 6 to 14 carbon atoms unsubstituted or substituted, heteroaryl unsubstituted or substituted and heterocyclic unsubstituted or substituted, W is selected from the group comsisting of $-(CH_2)_{n1}-$ or $-(CH_2)_{n2}-NY-(CH_2)_{n3}$, $n_1$, $n_2$ and $n_3$ are individually integers from 2 to 6, Y is selected from the group consisting of hydrogen, alkyl of 1 to 12 carbon atoms, aryl of 6 to 12 carbon atoms and aralkyl of 7 to 14 carbon atoms unsubstituted or substituted, $-COOAlk$ and $-COR_2$, Alk is alkyl of 1 to 12 carbon atoms, $R_2$ is selected from the group consisting of alkyl of 1 to 12 carbon atoms, alkenyl and alkynyl of 2 to 12 carbon atoms, aryl of 6 to 14 carbon atoms, aralkyl of 7 to 18 carbon atoms unsubstituted or substituted and heterocyclic unsubstituted or substituted, Z is selected from the group consisting of hydrogen,

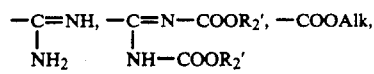

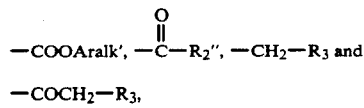

$-COCH_2-R_3$, $R_2$ is alkyl of 1 to 12 carbon atoms or aralkyl of 7 to 18 carbon atoms, Alk' is alkyl of 1 to 12 carbon atoms, ArAlk is aralkyl of 7 to 18 carbon atoms, $R_2'$ is $R_2$, $R_3$ and $R_3'$ are selected from the group consisting of aryl substituted or unsubstituted, heteroaryl substituted or unsubstituted, heterocyclic unsubstituted or substituted and $R_1$ with the proviso that Z is not hydrogen when W is $-(CH_2)_3-$ and $R_1$ is 2,4-dichlorophenoxy and their non-toxic, pharmaceutically acceptable acid addition salts having fungicidal activity.

16 Claims, No Drawings

ACYLATED AMINE COMPOUNDS WHICH ARE USEFUL FUNGICIGAL AGENTS

STATE OF THE ART

Related prior art includes U.S. Pat. No. 3,282,673; French Pat. Nos. 2,306,683; 1,4555,055 and 1,140,070; U.S. Pat. Nos. 4,518,783 and 4,350,634; Canadian Journal of Chemistry, Vol. 62 (1984), p. 967 to 974, Tetrahedron Letters Vol. 25 No. 50 (1984), p. 5725 to 5728, Chem. Abs., Vol. 86 (1977), p. 508, No. 106546y and Chem. Abs., Vol. 69 (1968), p. 2600 to 260 1, No. 27754k.

OBJECTS OF THE INVENTION

It is an object of the invention to provide the novel compounds of formula I and their non-toxic, pharmaceutically acceptable acid addition salts and their preparation and intermediates.

It is another object of the invention to provide novel fungicidal compositions and a novel method of combatting fungi.

These and other objects and advantages of the invention will become obvious from the following detailed description.

THE INVENTION

The novel compounds of the invention are selected from the group consisting of a compound of the formula

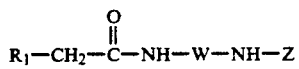

wherein $R_1$ is selected from the group consisting of Ar—O— and aryl, polyaryl and condensed polyaryl unsubstituted or substituted and heterocycle unsubstituted or substituted, Ar is aryl of 6 to 14 carbon atoms unsubstituted or substituted, heteroaryl unsubstituted or substituted and heterocyclic unsubstituted or substituted, W is selected from the group consisting of —(CH$_2$)$_{n1}$— or —(CH$_2$)$_{n2}$—NY—(CH$_2$)$_{n3}$, $n_1$, $n_2$ and $n_3$ are individually integers from 2 to 6, Y is selected from the group consisting of hydrogen, alkyl of 1 to 12 carbon atoms, aryl of 6 to 12 carbon atoms and aralkyl of 7 to 14 carbon atoms unsubstituted or substituted, —COOAlk and —COR$_2$, Alk is alkyl of 1 to 12 carbon atoms, R$_2$ is selected from the group consisting of alkyl of 1 to 12 carbon atoms, alkenyl and alkynyl of 2 to 12 carbon atoms, aryl of 6 to 14 carbon atoms, aralkyl of 7 to 18 carbon atoms unsubstituted or substituted and heterocyclic unsubstituted or substituted, Z is selected from the group consisting of hydrogen,

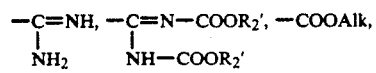

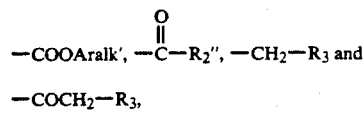

R'$_2$ is alkyl of 1 to 12 carbon atoms or aralkyl of 7 to 18 carbon atoms, Alk' is alkyl of 1 to 12 carbon atoms, ArAlk is aralkyl of 7 to 18 carbon atoms, R'$_2$ is R$_2$, R$_3$ and R'$_3$ are selected from the group consisting of aryl substituted or unsubstituted, heteroaryl substituted or unsubstituted, heterocyclic unsubstituted or substituted and R$_1$ with the proviso that Z is not hydrogen when W is —(CH$_2$)$_3$— and R$_1$ is 2,4-dichlorophenoxy and their non-toxic, pharmaceutically acceptable acid addition salts.

A preferred groups of compounds are those of the formula

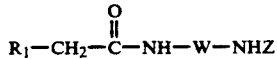

wherein $R_1$ is selected from the group consisting of ArO—, Ar is unsubstituted or substituted heteroaryl or substituted or unsubstituted heterocyclic or substituted or unsubstituted aryl of 6 to 14 carbon atoms and a condensed or non-condensed aryl, polyaryl and substituted or unsubstituted heterocyclic, W is

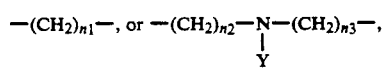

$n_1$ is an integer from 3 to 6, $n_2$ and $n_3$ are individually integers from 2 to 6, Y is selected from the group consisting of hydrogen, alkyl of 1 to 12 carbon atoms, substituted or substituted aryl of 6 to 14 carbon atoms, substituted or unsubstituted aralkyl of 7 to 18 carbon atoms, —COOAlk and —COR$_2$, Alk is alkyl of 1 to 12 carbon atoms, R$_2$ is selected from the group consisting of alkyl of 1 to 12 carbon atoms, alkenyl and alkynyl of 2 to 12 carbon atoms, aryl of 6 to 14 carbon atoms, substituted or unsubstituted aralkyl of 7 to 18 carbon atoms and substituted or unsubstituted heterocycle, Z is selected from the group consisting of

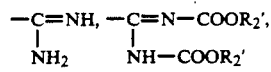

—COOAlk, —COOArAlk, —CH$_2$R$_3$ and —COCH$_2$—R'$_3$, R'$_2$ is alkyl of 1 to 12 carbon atoms or aralkyl of 7 to 18 carbon atoms, Alk has the above definition, ArAlk is aralkyl of 7 to 18 carbon atoms, R$_3$ is optionally substituted aryl or optionally substituted heteroaryl or optionally substituted heterocycle or R$_1$ and R'$_3$ is R$_3$, with the provisio that if W is —(CH$_2$)$_3$— and R$_1$ is 2,4-dichlorophenoxy, R$_1$ is not 2,5-dihydroxyphenyl or 2,5-dimethoxyphenyl and Z is not hydrogen and their non-toxic, pharmaceutically acceptable acid addition salts.

Examples of suitable acids for their non-toxic, pharmaceutically acceptable acid addition salts are inorganic acids such as hydrochloric acid, hydrobromic acid, hydroiodic acid, nitric acid, sulfuric acid or phosphoric acid or organic acids such as formic acid, acetic acid, propionic acid, trifluoroacetic acid, benzoic acid, maleic acid, fumaric acid, succinic acid, tartaric acid, citric acid, oxalic acid, glyoxylic acid, aspartic acid, alkanesulfonic acids such as methane sulfonic acid and ethane sulfonic acid and arylsulfonic acids such as benzene sulfonic acid or p-toluene sulfonic acid.

In the definition of the various substituents: aryl preferably is phenyl; polyaryl preferably is naphthyl or biphenyl; alkyl preferably is methyl, ethyl, n-propyl, isopropyl, n-butyl, isobutyl, sec-butyl or tert-butyl; alkenyl preferably is vinyl, allyl or 1,1-dimethylallyl; alkynyl preferably is ethynyl or propynyl.

The heterocyclics are preferably pyridyl, furanyl, thiophenyl, indolyl, coumarinyl, oxazolyl, thiazolyl or a 7-(3,7-dihydro-1,3-dimethyl-2,6-dioxo)-1H-purinyl. The aryl alkyl of W and Z, when they are substituted, are preferably substituted by hydroxyl, halogen such as chlorine or bromine, $CF_3$ or alkoxy of 1 to 4 carbon atoms for example, methoxy.

More particularly are the compounds of formula I in which the aryl, heteroaryl, arylalkyl and heterocyclic radicals are optionally substituted by at least one substituent selected from the group consisting of hydroxyl, halogen, alkyl, alkenyl and alkynyl of up to 12 carbon atoms, aryl of 6 to 14 carbon atoms, $-CF_3$, $-OR_3$ in which $R''_3$ is alkyl of 1 to 12 carbon atoms or arylalkyl of 7 to 18 carbon atoms, COalkyl, $-Si(alkyl)_3$, $-SO_2$alkyl in which the alkyl contains 1 to 12 carbon atoms, and $-SO_2$aryl in which the aryl contains 6 to 14 carbon atoms, the various groups being able between them to form, with the atoms to which they are linked, O—CH$_2$—O rings, as well as their non-toxic, pharmaceutically acceptable addition salts with organic or mineral acids.

Among the preferred compounds of the invention are those wherein W is $-(CH_2)_3-$, $-(CH_2)_4-$ or $-(CH_2)_5-$ or $-(CH_2)_{n_4}NH(CH_2)_{n_5}-$ in which $n_4$ and $n_5$ individually are 3, 4 or 5, as well as their addition salts with organic or mineral acids. More preferably are the compounds of formula I wherein Z is hydrogen or $CO_2$alkyl in which the alkyl contains 1 to 12 carbon atoms or

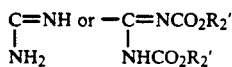

$R'_2$ keeping the same meaning as above, as well as their addition salts with organic mineral acids.

A preferred group of compounds of formula I are those wherein $R_1$ is ArO— in which Ar is an optionally substituted aryl such as for example:

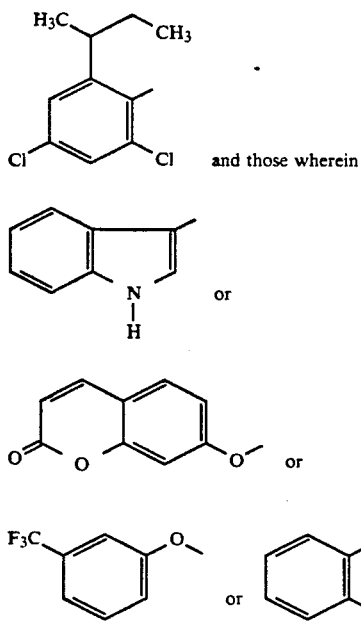

and those wherein as well as their addition salts with organic or mineral acids.

Specific preferred compounds of the invention are N-[(6-sec-butyl-2,4-dichlorophenoxy)-acetyl]-1,4-diamino-butane, 3,3'-[N-(6-sec-butyl-2,4-dichlorophenoxy)-acetyl]-3,3'-diaminodipropylamine, N-(7-acetoxy-coumarinyl)-1,4-diamino-butane, N-[(6-sec-butyl-2,4-dichlorophenoxy)-acetyl]-N,N-spermidine, N-[(6-sec-butyl-2,4-dichlorophenoxy)-acetyl]-4-guanidine-aminobutane, N-[(6-sec-butyl-2,4-dichlorophenoxy)-acetyl]-1,3-diamino-propane, N-[(6-sec-butyl-2,4-dichlorophenoxy)-acetyl]-1,5-diamino-pentane, and their non-toxic, pharmaceutically acceptable acid addition salts.

The novel process of the invention for the preparation of compounds of formula I comprises reacting an acid of the formula $$R_1CH_2CO_2H \qquad \qquad II$$

in which $R_1$ has the above definition or a functional derivative thereof with a polyamine of the formula $$NH_2-W-NH-Z \qquad \qquad III$$

in which W and Z have the above definitions to obtain the corresponding compound of formula I, which is subjected, if desired, wherein Z is hydrogen to the action of an agent for functionalizing the amine function, then if desired, the compound of formula I obtained is subjected to the action of an acid to form the salt.

This direct acylation of the amine NH$_2$(W)NHZ by the acid $R_1CH_2CO_2H$ can be done directly by heating or by activation of the acid function using for example dicyclohexylcarbodiimide, N,N'-carbonyldiimidazole or diethylcyanophosphonate or also by the intermediary of the derivatives of the acid according to the reaction:

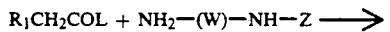

L being one of the following:
L=Cl or OCOR'

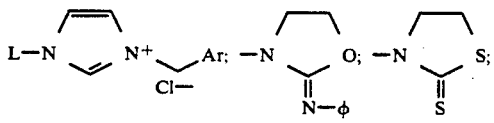

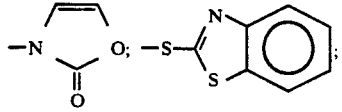

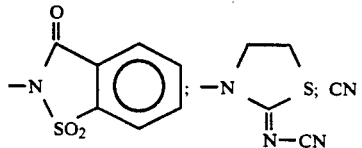

See on this subject the works of: March "Advanced Organic Chemistry" Sec. Ed. p. 384; Albertson, Org.

React., Vol. 12, p. 205 to 218 (1962); Klausner et al., Synthesis, p 453 (1972); Paul et al., J. Am. Chem. Soc., Vol. 82, p 4596, (1960); Tetrahedron Lett. p. 1595 (1973); Tetrahedron Vol. 32, p. 221 (1976); Beckwit "Chemistry of Amides" Ed. Zabicky 73-185 (1970); Sonntag, Chem. Rev., Vol. 52, p. 237 to 416 (1953); Chem. Pharm. Bull (1982), Vol. 30 p. 4242; Bull. Chem. Soc. Fr (1982) p. 11, 167; Tetrahedron Lett. (1980) Vol. 21, p. 841; Tetrahedron Lett. (1985) Vol. 26, 1977; Synthesis (1982), p. 933; Chem. Lett. (1985) p. 123; Heterocycles (1988); Vol. 27, p. 323; and Chem. Lett. (1987), p. 879 to 882.

The compounds of formula III are generally known and can be prepared in a standard way by processes described by Green, Protective Groups in Organic Synthesis, Wiley Ed., Hoppe Seyler's Physiol. Chem., Vol. 357, p. 1651 (1976); Bergeron et al., Synthesis (1982), Bergeron et al., J. Org. Chem., Vol. 49, p 2997; Atwell et al., Synthesis, (1984) p. 10373. Some products of formula III in which W is —(CH$_2$)$_{n4}$NH(CH$_2$)$_{n5}$— and n$_4$ and n$_5$ are defined as previously, as well as those for which Z is CH=N—COOR$_2$ and W is —(CH$_2$)$_n$— with n varying from 2 to 6, are new products and are one of the subjects of the present invention. Their preparation is given hereafter in the experimental part.

A variation of the process of the invention in which R$_1$ is ArO— comprises reacting a compound of the formula

ArOH     VI with a compound of the formula

Hal—CH$_2$—CO—NH—W—NHZ     VII in which W and Z have the above definition and Hal is halogen to obtain the corresponding compound of the formula

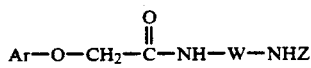
$$Ar-O-CH_2-\overset{\overset{O}{\|}}{C}-NH-W-NHZ \quad I_B$$

which is subjected, if desired, to the action of an acid to form its salt.

The compounds of formula VII used as starting products are new products and are an object of the invention and their preparation is given hereafter in the experimental part. It can be summarized by the following schemes:

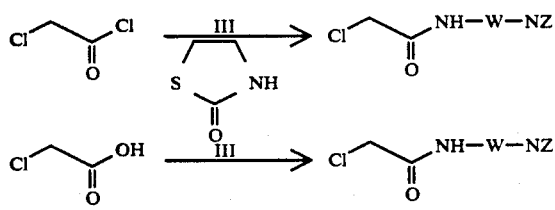

The novel fungicidal compositions of the invention are comprised of a fungicidally effective amount of at least one compound of formula I and their acid addition salts and an inert carrier. The compositions may be in the form of powders, granules, suspensions, emulsions, solutions or other usual forms employed for this purpose.

Examples of suitable inert carriers are non-ionic surface-active vehicle and/or agent to ensure a uniform dispersion of the substances in the mixture. The vehicle used can be a liquid such as water, alcohol, hydrocarbons or other organic solvents, a mineral, animal or vegetable oil, a powder such as talc, clays, silicates, kieselguhr or a combustible solid.

Naturally the compositions can contain one or more other pesticide agents, for example one or more insecticide or acaricide agents.

The compositions have very useful fungicidal properties which can be used for protection against pathogenic fungi for protection of plants, protection of premises or protection of a animals and can be used in human and animal hygiene and medicine.

The compositions of the invention are useful in combating a great number of phytopathogenic fungi, particularly the combatting of: *Erysiphe graminis, Sphaerotheca macularis, Sphaerotheca fuliginea, Podosphaera leucotricha, Uncinula necator*, Helminthosporium spp., Rhynchosporium spp., Septoria spp., *Pseudocercosporella herpotrichoides* and *Gaeumannomyces graminis*, Ustilago spp., *Cercospora arachidicola* and *Cercosporidium personatum*, Cercospora species, *Botrytis cinera*, Alternaria spp., *Venturia inaequalis, Plasmopara viticola, Bremia lactucae*, Peronospora spp., *pseudoperonospora humuli, Pseudoperonospora cubensis*, Phytophtora spp., infestans, Phytophthora spp., *Thanatephorus cucumeris*, Rhizoctonia spp., or also fungi or yeasts affecting human health such as *Candida albicans* or Trychophyton spp.

The novel method of the invention for combatting fungi comprises contacting fungi with a fungicidally effective amount of at least one compound of formula I and its acid addition salts.

In the following examples there are described several preferred embodiments to illustrate the invention. However, it should be understood that the invention is not intended to be limited to the specific embodiments.

EXAMPLE 1

N-[(6-sec-butyl-2,4-dichlorophenoxy)-acetyl]-1,4-diamino-butane

STEP A: 6-sec-butyl-2,4-dichloro-phenol

A mixture of 62.76 g of 6-sec-butyl-phenol and 75 ml of sulfuryl chloride was refluxed with stirring for 90 minutes and after returning to room temperature, the mixture was poured into 400 ml of water. The mixture was extracted with methylene chloride and the organic phase was evaporated to dryness under reduced pressure. The 89.9 g of oil residue were distilled at 82° C. and 0.01 mm Hg to obtain 27.8 g of the desired product.

STEP B: Ethyl 6-sec-butyl-2,4-dichlorophenoxy acetate 2.8 ml of ethyl bromoacetate were added at room temperature to a mixture of 5 g of the product of Step A and 20 ml of dimethylsulfoxide and 4.45 g of potassium carbonate were added in portions to the resulting solution. The solution was heated at 70° to 80° C. for 3 hours and was then poured into an ice-water mixture. The mixture was extracted with methylene chloride and the organic phase was evaporated to dryness under reduced pressure. The residue was chromatographed over silica and was eluted with a 97-3 hexane-ethyl acetate mixture to obtain 6.58 g of the desired product.

STEP C: 6-sec-butyl-2,4-dichlorophenoxy-acetic acid

A mixture of 6.5 g of the product of Step B, 15 ml of ethanol and 10.65 ml of 2N sodium hydroxide was stirred at 20° C. for one hour and then 10.65 ml of 2N hydrochloric acid were added. The mixture was evaporated to dryness under reduced pressure and the 10 g of residue were taken up in 200 ml of water. The mixture was vacuum filtered and dried to obtain 5.83 g of the desired product.

STEP D: 6-sec-butyl-2,4-dichlorophenoxy-acetyl chloride

A mixture of 5.8 g of the product of Step C and 40 ml of thionyl chloride was refluxed for 2 hours and was evaporated to dryness under reduced pressure. The oil residue was washed with benzene and evaporated to dryness under reduced pressure to obtain 6.2 g of the desired product which was used as is for the next step.

STEP E: N-(tert.-butoxycarbonyl)-1,4-diamino-butane

A solution of 400 g of ditertbutoxycarbonyl oxide in 2000 ml of methylene chloride was added over one hour at 0° to 5° C. to a solution of 320 g of 1,4-diamino-butane in 2800 ml of methylene chloride and the mixture was stirred at 20° C. for 1 hour and was filtered. The filtrate was evaporated to dryness under reduced pressure and the 363.1 g of residue were chromatographed over silica. Elution with a 9-1 flugene-methanol mixture, then with methanol and finally with a 96-4 methanol-ammonium, hydroxide mixture yielded 203.6 g of the desired product.

NMR Spectrum (CDCl$_3$): 87 Hz (t.butyl); 162 Hz (CH$_2$NH$_2$); 186 Hz (CH$_2$NHCO); 280 Hz (C═O); 89 Hz (central CH$_2$).

STEP F:
N-(tert.butoxycarbonyl)-N'-[(6-sec-butyl-2,4-dichlorophenoxy)-acetyl]-1,4-diamino-butane A suspension of 6.2 g of the product of Step D in 50 ml of chloroform was added at 10° C. to a mixture of 3.95 g of the product of Step E, 40 ml of chloroform and 3 ml of triethylamine and the mixture was stirred at room temperature for one hour and was evaporated to dryness under reduced pressure. The residue was taken up in tetrahydrofuran and the mixture was filtered. The filtrate was evaporated to dryness under reduced pressure and the 10.15 g of residue was chromatographed over silica. Elution with a 7-3 hexane-ethyl acetate mixture to obtain 8.42 g of the desired product melting at 50° C.

STEP G:
N-[(6-sec-butyl-2,4-dichlorophenoxy)-acetyl]-1,4-diamino butane

A mixture of 8.12 g of the product of Step F, 80 ml of ethanol and 20.1 ml of ethanolic, 2N hydrogen chloride was refluxed with stirring for one hour and was evaporated to dryness under reduced pressure. The residue was washed with methylene chloride to obtain 6.7 g of the desired hydrochloride. A mixture of 6.7 g of the hydrochloride, 100 ml of ethanol and 3.2 g of sodium bicarbonate was refluxed with stirring for 4 hours and the mixture was filtered hot. The filtrate was evaporated to dryness under reduced pressure and the 6.05 g of residue was chromatographed over silica. Elution with a 98-2 methanol-ammonium hydroxide yielded 4.74 g of the desired product.

Analysis: C$_{16}$H$_{24}$Cl$_2$N$_2$O$_2$ Calculated: %C 55.34; %H 6.96; %N 8.07; %Cl 20.42; Found: %C 55.2; %H 7.1; %N 7.8; %Cl 19.5.

EXAMPLE 2

N-[1-(3-indolyl)-acetyl]-1,4-diamino-butane

STEP A: 1,3-indolyl acetyl chloride

A suspension of 27 g of phosphorus pentachloride and 500 ml of ether was stirred at 0° C. and 20 g of indole acetic acid were slowly added thereto. The mixture was stirred at 0° C. for 15 minutes and was reduced under reduced pressure to a volume of 200 ml. 2 liters of hexane were added and after stirring for two hours, the mixture was vacuum filtered. The product was dried under reduced pressure to obtain 8.38 g of the desired product melting at 66° C.

STEP B:
N-(tert-butoxycarbonyl)-N'-[1-(3-indolyl)-acetyl]-1,4-diamino-butane Using the procedure of Step F of Example 1, 8.10 g of the product of Step E of Example 1 and 8.39 g of the product of Step A in methylene chloride were reacted and the dry extract was taken up in tetrahydrofuran. The mixture was filtered and the filtrate was evaporated to dryness. The 16.53 g of residue were chromatographed over silica and eluted with a 98-2 chloroform-methanol mixture, then with a 7-3 ethyl acetate-hexane mixture and finally with ethyl acetate to obtain 11.47 g of the desired product.

Analysis: C$_{19}$H$_{27}$N$_3$O$_3$ Calculated: %C 66.06; %H 7.88; %N 12.16; Found: %C 65.8; %H 8.0; %N 11.9.

STEP C: N-[1-(3-indolyl)-acetyl]-1,4-diamino-butane

Using the procedure of Step G of Example 1, 9.35 g of the product of Step B and 35 ml of ethanolic 1N hydrogen chloride were reacted to obtain after double chromatography 2.28 g of the desired base.

Analysis: Calculated: %C 68.54; %H 7.81; %N 17.13; Found: %C 68.2; %H 7.9; %N 16.6.

EXAMPLE 3

N-(7-acetoxy-coumarinyl)-1,4-diamino-butane

STEP A: Chloroacetyl N-(tert-butoxycarbonyl)-1,4-diamino-butane

A solution of 5.65 g of chloroacetyl chloride in 50 ml of tetrahydrofuran was added with stirring at 0° C. to a mixture of 9.4 g of the product of Step D of Example 1, 7.3 ml of triethylamine and 100 ml of tetrahydrofuran and after stirring for 2 hours, the mixture was evaporated to dryness under reduced pressure. The residue was taken up in 100 ml of methylene chloride and 50 ml of water and the decanted organic phase was evaporated to dryness under reduced pressure to obtain 12 g of the expected product melting at 98° to 100° C.

STEP B:
N-(tert-butoxycarbonyl)-N'-(7-acetoxy-coumarinyl)-1,4-diamino-butane 2.96 g of sodium hydride in 50% of oil were added at room temperature to a solution of 10 g of 7-hydroxy-coumarine in 100 ml of dimethylformamide and after stirring at room temperature for 45 minutes, a solution of 17.98 g of the product of Step A in 60 ml of dimethylformamide was added. The solution was stirred for 5 hours at 90° C. and 60 hours at room temperature and then was evaporated to dryness under reduced pressure. The 37.6 g of residue were taken up in 180 ml of water and was vacuum filtered. The product was empasted with isopropyl ether to obtain 23.25 g of the desired product melting at 120° C.

STEP C: N-(7-acetoxy-coumarinyl)-1,4-diamino-butane hydrochloride

A mixture of 19.85 g of the product of Step B in 200 ml of ethanol and 38.1 ml of ethanolic 2N hydrogen chloride was refluxed with stirring for one hour and was then evaporated to dryness to obtain 18.67 g of raw product melting at 90° C. The product was crystallized from a refluxing mixture of 95-5 acetonitrile and water and was vacuum filtered. The product was empasted with isopropyl ether to obtain 8.44 g of the desired product melting at 160° C.

Analysis: $C_{15}H_{19}ClN_2O_4$ (4.8% water) Calculated: %C 55.13; %H 5.86; %N 8.57; %Cl 10.85; Found: %C 52.3; %H 6.2; %N 8.2; %Cl 10.6.

EXAMPLE 4

N-[(3-trifluoromethylphenoxy)-acetyl]-1,4-diamino-butane

STEP A: Ethyl 3-trifluoromethyl phenoxy-acetate 15 ml of ethyl bromoacetate were added to a mixture of 15 ml of 3-trifluoromethyl-cresol and 60 ml of dimethylsulfoxide and then 24 g of potassium carbonate were added portionwise. The mixture was heated at 70° to 80° C. for 5 hours and then poured into 400 ml of an ice-water mixture. The mixture was extracted with methylene chloride and the organic phase was evaporated to dryness. The residue was taken up in dilute sodium hydroxide and was extracted with methylene chloride. The organic phase was evaporated to dryness under reduced pressure to obtain 28.61 g of the product which was used as is for the next step.

STEP B: 3-trifluoromethyl-phenoxy-acetic acid

A solution of 23.2 g of the product of Step A, 50 ml of ethanol and 47 ml of 2N sodium hydroxide solution was stirred for one hour and 47 ml of 2N hydrochloric acid were added. The mixture was evaporated to dryness under reduced pressure and the residue was taken up in water and vacuum filtered to obtain 19.73 g of the desired product melting at 96° C.

STEP C: 3-trifluoromethyl-phenoxy-acetyl chloride

A solution of 6 g of the product of Step B in 36 ml of thionyl chloride was refluxed with stirring for one hour and was evaporated to dryness under reduced pressure to obtain 6.44 g of the desired product which was used as is for the next step.

STEP D:
N-(tert-butoxycarbonyl)-N'-(3-trifluoromethyl-phenoxy-acetyl)-1,4-diamino butane A solution of 6.44 g of the product of Step C in 60 ml of chloroform was added at +10° C. to a solution of 10.2 g of N-(tert-butoxycarbonyl)-1,4-diamino-butane in 150 ml of chloroform and after stirring for 2 hours at room temperature, the mixture was evaporated to dryness under reduced pressure. The product was added to water and vacuum filtered to obtain 7.85 g of the desired product melting at 86° C.

STEP E: N-(3-trifluoromethyl phenoxy acetyl)-1,4-diamino-butane hydrochloride

A mixture of 9.8 g of the product of Step D, 90 ml of ethanol and 28 ml of ethanolic 2N hydrogen chloride was refluxed with stirring for one hour and then evaporated to dryness under reduced pressure to obtain 11.9 g of product which was crystallized from ethyl acetate to obtain 7.55 g of the desired product melting at 90° C.

Analysis: $C_{13}H_{18}ClF_3N_2O_2$ (2.6% hydrated with water) Calculated: %C 47.79; %H 5.55; %F 10.85; %Cl 17.44; %n 8.57; Found: %C 47.0; %H 5.7; %F 10.5; %Cl 17.0; %n 8.1.

EXAMPLE 5

N-(3-trifluoromethyl phenoxy acetyl)-N'-[1-(3-indol acetyl)]-1,4-diamino-butane 3.72 g of 3-indole acetic acid were added to a mixture of 6.44 g of 2-chloro-N-methyl-pyridinium iodide in 100 ml of tetrahydrofuran and then a solution of 6 g of the product of Example 4 in 150 ml of tetrahydrofuran was slowly added thereto. 7 ml of triethylamine were added and the mixture was stirred at reflux for 6 hours and at room temperature for 16 hours. The mixture was evaporated to dryness under reduced pressure and the 16.7 g of residue were chromatographed over silica. Elution with a 1-1 methylene chloride-tetrahydrofuran mixture yielded 6.19 g of the expected product.

Analysis: $C_{23}H_{24}F_3N_3O_3$ Calculated: %C 61.74; %H 5.41; %F 12.74; %N 9.39; Found: %C 61.4; %H 5.5; %F 12.1; %N 9.4.

EXAMPLE 6

3,3'-[N-(6-sec-butyl-2,4-dichloro-phenoxy)-acetyl]-3,3'-diaminodipropyamine dihydrochloride STEP A: N-(tert-butoxycarbonyl)-(3-amino propyl)-1,3-propanediamine A solution of 33 g of tert-butyl dicarbonate in 200 ml of methylene chloride was added at 5° C. to a solution of 39.3 g of 3,3'-diaminodipropylamine in 300 ml of methylene chloride and after stirringf or 16 hours at 20° C., water was added, followed by decanting and evaporation to dryness. The residue was chromatographed on silica (eluant; methanol-ammonia (98-2)) to obtain 15.5 g of the expected product which was used as is for the next step.

STEP B:
N-[(6-sec-butyl-2,4-dichloro-phenoxy)-acetyl]-thiazolidine-2-thione

A solution of 8.09 g of dicyclohexylcarbodiimide and 340 mg of 4-dimethylamino-pyridine in 60 ml of methylene chloride was added at −5°/0° C. to a solution of 9.78 g of (6-sec-butyl-2,4-dichloro phenoxy) acetic acid and 4.63 g of 2-mercaptothiazoline in 80 ml of methylene chloride and the mixture was stirred for 10 minutes at 0° C. and for four hours at ambient temperature. After filtering off the insolubles, the filtrate was evaporated to dryness, and the residue was chromatographed on silica (eluant: hexane-ethyl (7-3)) to obtain 10.3 g of expected product melting at 96° C.

STEP C:
3,3'-[N-[(6-sec-butyl-2,4-dichloro-phenoxy)-acetyl]-N''-(tert-butoxycarbonyl)]3,3'-diaminodipropylamine A solution of 2.6 g of the product of Step B in 25 ml of methylene chloride was added at 0° C. to a solution of 1.59 g of the product of Step A in 15 ml of methylene chloride and the mixture was stirred for 45 minutes at ambient temperature and evaporated to dryness. The residue was chromatographed on silica (eluant: methanol) to obtain 3.19 g of the expected product.

STEP D:
3,3'[N-(6-sec-butyl-2,4-dichloro-phenoxy)-acetyl]-3,3'-diaminodipropylamine dihydrochloride 6.4 ml of a 2.25N solution of ethanolic hydrogen chloride were added to a solution of 3.19 g of the product of Step C in 30 ml of ethanol and the mixture was refluxed for one hour and evaporated to dryness under reduced pressure. The residue was triturated with isopropyl ether to obtain 2.58 g of the expected product melting at 196° C.

Analysis: $C_{18}H_{31}O_2N_3Cl_4$, hydrated with 2% water:
Calculated: %C 46.67; %H 6.74; %Cl 30.61; %N 9.7;
Found: %C 46.0; %H 6.9; %Cl 29.9; %N 9.0.

EXAMPLE 7
N-[(6-sec-butyl-2,4-dichlorophenoxy)-acetyl]-4-guanidine-aminobutane trifluoroacetate

STEP A: N-benzyloxy carbonyl 1,4-diamino butane

A solution of 46 g of methane sulfonic acid in 50 ml of water was added without exceeding 30° C. to a mixture of 23 g of 1,4-diamino butane and 50 ml of water and the reaction medium was diluted with 140 ml of ethanol. A solution of 39 g of benzyl chloroformate in 50 ml of 1,2-dimethoxy ethane and 100 ml of a 50% aqueous solution of potassium acetate were added alternately at pH 3.5 to 5.0. The additions were made alternately to maintain the pH value between 3.5 and 5.0. The mixture was stirred for 90 minutes at 20° to 25° C. and evaporated under reduced pressure. The residue was poured over 500 ml of water and the insoluble part was filtered off. The filtrate was washed 3 times with 150 ml of benzene, and then 100 ml of 30% sodium hydroxide saturated with sodium chloride were added. After extraction with benzene, the extracts were evaporated to dryness under reduced pressure to obtain 19.10 g of the expected product.

STEP B: N,N'-bis-(tert-butoxycarbonyl)-methyl thioisourea 58.1 g of tert-butyl dicarbonate, 25.3 g of methyl thioisourea sulfate, 50 g of sodium bicarbonate, 500 ml of water and 500 ml of methylene chloride were stirred for 48 hours at 20° C. and after decanting, followed by extraction with methylene chloride and evaporation to dryness, 27 g of the expected product melting at 118° C. were obtained.

STEP C: $N_1$-($N'_1$, $N'_2$-bis-tert-butoxycarbonyl formamidino)-$N_2$-carbobenzyloxy-1,4-diamino butane A mixture of 13.4 g of product obtained in Step A, 14.5 g of N,N'-bis-(tert-butoxycarbonyl)-methyl thioisourea of Step B and 100 ml of tetrahydrofuran was refluxed with stirring for 2 hours and the mixture was concentrated under reduced pressure. The residue was taken up in 200 ml of chloroform, washed with 30 ml of a saturated solution of sodium bicarbonate in water and concentrated to dryness under reduced pressure. Chromatography was carried out on silica (eluant: ethyl acetate) to obtain 12.7 g of the expected product.

STEP D: $N_1$-($N_1$,$N_2$-bis-tert-butoxycarbonyl formamidino)-1,4-diamino butane 1 g of active charcoal with 10% palladium was added to a solution of 12.7 g of the product of Step C in 100 ml of ethanol with stirring under hydrogen pressure until absorption was completed. The catalyst was filtered off and the filtrate was evaporated to dryness under reduced pressure to obtain 6.6 g of the expected product.

| NMR (CDCl$_3$) | | |
|---|---|---|
| 2.74 (m) | 2H | } N—CH$_2$ |
| 3.43 (m) | 2H | |
| 1.5 (s) | | } COOtBu |
| 1.51 (s) | | |
| 1.5 to 1.8 (m) central CH$_2$'s | | |
| 8.35 | | } mobile proton |
| 11.5 | | |

STEP E:
N-[(6-sec-buty-2,4-dichlorophenoxy)-acetyl]-4-(di-tert-butoxycarbonyl guanidine)-aminobutane 3.43 g of the product of Step B of Example 6 in solution in 40 ml of methylene chloride were added at 0° C. to a solution of 4.89 g of N-(di-tert-butoxycarbonyl guanidine) aminobutane in 50 ml of methylene chloride and the mixture was stirred for one hour at ambient temperature, then brought to dryness. The residue was chromatographed on silica (eluant: hexane-ethyl acetate (7-3) with 1% triethylamine) to obtain 3.63 g of the expected product.

STEP F:
N-[(6-sec-butyl-2,4-dichlorophenoxy)-acetyl]-4-guanidine-aminobutane trifluoroacetate 2.4 ml of trifluoroacetic acid were added at ambient temperature to a solution of 1.82 g of the product of Step E in methylene chloride and after stirring for 48 hours and evaporation to dryness under reduced pressure, 1.56 g of the expected product were obtained.

Analysis: $C_{17}H_{31}N_4O_2Cl_2$, 1.25M $CF_3CO_2H$
solvated by 1.25 mol of trifluoroacetic acid Calculated: %C 45.34; %H 5.4; %N 11.13; %Cl 14.09; %F 11.32; Found: %C 44.03; %H 5.16; %N 10.53; %Cl 13.33; %F 13.4.

EXAMPLE 8
N-[(6-sec-butyl-2,4-dichlorophenoxy)-acetyl]-N,N'spermidine dihydrochloride

STEP A: N-phthaloyl aminobutyraldehyde diethylacetal

A solution of 24.8 g of 4-aminobutyraldehyde diethylacetal in 250 ml of tetrahydrofuran was added at 20° C. to a solution of 30.1 g of N-carbethoxy-phthalimide in 150 ml of tetrahydrofuran and the mixture was refluxed with stirring for 3 hours. The solvent was evaporated off and the residue was chromatographed on silica (eluant: hexane-ethyl acetate (65-35)) to obtain 34.9 g of the expected product.

Analysis: $C_{16}H_{21}NO_4$ Calculated: %C 65.97; %H 7.26; %N 4.80; Found: %C 66.0; %H 7.2; %N 4.7.

STEP B: 4-phthalimido butanal 33.9 g of the product of Step A in 350 ml of 2N hydrochloric acid were stirred for 3 hours and after diluting with water, extraction was done with methylene chloride. The extracts were evaporated to dryness to obtain 24 g of the expected product melting at 70° C.

Analysis: $C_{16}H_{21}NO_4$ Calculated: %C 66.35; %H 5.1; %N 6.45; Found: %C 66.2; %H 4.9; %N 6.3.

STEP C:
N'-(phthaloyl)-N''-(tert-butoxycarbonyl)-spermidine 2.4 g of palladized charcoal were added to a solution of 8.68 g of the product of Step B, 7 g of N-(tert-butoxycarbonyl)-1,3-diamino propane in 120 ml of ethanol with stirring under a hydrogen atmosphere until absorption was completed. The catalyst was filtered off, the filtrate is evaporated to dryness and the residue was chromatographed on silica (eluant: methanol with 1% ammonia) to obtain 8.5 g of the expected product.

Analysis: $C_{20}H_{29}N_3O_4$ Calculated: %C 63.98; %H 7.78; %N 11.19; Found: %C 63.1; %H 8.2; %N 10.4.

STEP D: N-(tert-butoxycarbonyl)-spermidine 4.5 ml of 80% hydrazine hydrate were added to a solution of 8.5 g of the product of Step C in 250 ml of ethanol and the mixture was refluxed for one hour. The insoluble part was filtered off and the filtrate was evaporated to dryness under reduced pressure. The residue was taken up in methylene chloride, washed with water and evaporated to dryness under vacuum to obtain 4.13 g of the expected product.

| NMR (CDCl$_3$) | | | |
|---|---|---|---|
| 2.45–2.92 } | the N—CH$_2$'s | 1.42–1.83 central CH$_2$'s | |
| 3.05–3.36 | | 1.28 | NH$_2$ |
| 1.45–(S9H) | OtBu | 5.16 | NH |

STEP E:
N-[(6-sec-butyl-2,4-dichlorophenoxy)-acetyl]-N,N'-(tert-butoxycarbonyl)-spermidine Using the procedure of Step C of Example 6, 1.62 g of N,N'-tert-butoxycarbonyl spermidine and 2.5 g of N-[(6-sec-butyl-2,4-dichlorophenoxy)-acetyl]-thiazolidine-2-thione were reacted to obtain 2.64 g of the expected product.

STEP F:
N-[(6-sec-butyl-2,4-dichlorophenoxy)-acetyl]-N,N'-spermidine dihydrochloride Using the procedure of Step D of Example 6, 2.23 g of the expected product were obtained.

Analysis: $C_{19}H_{33}O_2N_3Cl_4$ (product hydrated at 2%)
Calculated: %C 47.8; %H 6.97; %N 8.8; %Cl 29.71;
Found: %C 46.7; %H 7.2; %N 8.7; %Cl 28.7.

EXAMPLE 9

N-(2,4-dichloro phenoxy acetyl)-1,4-diamino-butane hydrochloride

STEP A: 2,4-dichlorophenoxy acetyl chloride 46 ml of thionyl chloride were added over 30 minutes to a solution of 130 g of 2,4-dichlorophenoxy-acetic acid in 150 ml of benzene, and the mixture was refluxed for one hour. The solvent and the excess thionyl chloride were eliminated under reduced pressure and the residue was distilled under 0.1 mm of mercury to obtain 91.4 g of the sought product with a boiling point of 120° C. at 0.1 mm of mercury.

STEP B:
N-(tert-butoxycarbonyl)-N'-(2,4-dichlorophenoxy acetyl)-1,4-diamino butane 11 g of 2,4-dichlorophenoxy-acetic acid chloride in solution in 40 ml of methylene chloride were added without exceeding 25° C. to a mixture of 8.6 g of N-(tert-butoxycarbonyl)-1,4-diamino-butane, 120 ml of methylene chloride and 7 ml of triethylamine and the mixture was stirred for 30 minutes, then concentrated to dryness under reduced pressure. The residue was taken up in 200 ml of tetrahydrofuran and the insoluble part was filtered off. The filtrate was evaporated to dryness under reduced pressure to obtain 18.53 g of crude product melting at 107° C. which was crystallized from 740 ml of isopropyl ether to obtain 17.43 g of the expected product melting at 110° C. 5.39 g were chromatographed on silica (eluant: hexane-ethyl acetate (6-4)) to obtain 4.48 g of the sought product melting at 114° C.

Analysis: $C_{17}H_{24}Cl_2N_2O_4$ Calculated: %C 52.18; %H 6.18; %Cl 18.12; %N 7.16; Found: %C 52.1; %H 6.2; %Cl 18.3; %N 7.0.

STEP C: N-(2,4-dichlorophenoxy acetyl)-1,4-diamino butane hydrochloride 10.15 g of product of Step B, 120 ml of ethanol and 35 ml of a 1.5N solution of hydrochloric acid ethanol were refluxed with stirring for two hours and then concentrated under reduced pressure. The 12.56 g of crude product melting at 90° C. were crystallized from 15 volumes of an ethanol-ethyl acetate mixture (1-1) to obtain 5.88 g of the expected product melting at 140° C.

Analysis: $C_{12}H_{17}Cl_3N_2O_2$: Calculated: %C 43.98; %H 5.22; %Cl 32.46; %N 8.55; Found: %C 43.9; %H 5.3; %Cl 32.2; %N 8.5.

EXAMPLE 10

1-(2,4-dichlorophenoxy acetyl)-triaza-1,6,10-decane dihydrochloride

STEP A:
1-tert-butoxycarbonyl-10-(2,4-dichlorophenoxy acetyl)-triaza-1,6,10-decane A solution of 4.5 g of 3-[(tert-butoxycarbonyl)-amino]-1-bromo-propane in 18 ml of tert-butanol was added to a mixture of 5.82 g of the product of Step C of Example 9 with 2.76 g of potassium carbonate and 30 ml of tert-butanol at reflux. After 5 hours of reflux, the mixture was cooled and the insoluble part was filtered off. The filtrate was evaporated to dryness and the 11.6 g of residue were chromatographed on silica (eluant: methanol) to obtain 3.44 g of the expected product.

STEP B: 1-(2,4-dichlorophenoxy acetyl)-triaza-1,6,10-decane dihydrochloride

A mixture of 3.44 g of the product of Step A, 100 ml of ethanol and 13 ml of a solution of about 2N of hydrochloric ethanol was refluxed with stirring for 4 hours and the mixture was cooled and separated to obtain 2.4 g of the expected product melting at 220° C.

Analysis: $C_{15}H_{23}Cl_2N_3O_2$, HCl Calculated: %C 42.77; %H 5.98; %N 9.98; %Cl 33.67; Found: %C 42.8; %H 6.0; %N 9.9; %Cl 33.2.

EXAMPLE 11

1,10-bis-(2,4-dichlorophenoxy acetyl)-6-methyl-triaza-1,6,10-decane

STEP A: 3-methyl-3-aza-1,6-dicyano hexane 75 g of 4-bromo-butyronitrile were added to a stirred mixture at 20° C. of 42 g of methylamino propionitrile, 325 ml of tert-butyl alcohol and 70 g of potassium carbonate and the mixture was refluxed with stirring for 2 hours, then for 16 hours at ambient temperature. The insoluble part was filtered off and the filtrate was concentrated. The 96 g of residue were chromatographed on silica (eluant: chloroform-acetone-cyclohexane (1-1-1) to obtain 54 g of the expected product.

| NMR (CDCl$_3$): | |
| --- | --- |
| 95 to 120.5 Hz | central CH$_2$'s |
| 137 Hz | N—CH$_3$ |
| 137 to 182 Hz | the other CH$_2$'s |

STEP B: 6-methyl-triaza-1,6,10-decane 10 g of the product of Step A, 20 ml of ethanol and 2 g of Raney's nickel were added to a solution of 3 g of sodium pellets in 55 ml of 95° ethanol, and the mixture was stirred in a hydrogen atmosphere until absorption was complete. The catalyst was filtered off and the filtrate was concentrated to a small volume, then 60 ml of water were added. After salting out with sodium hydroxide solution, the oil separated was collected and the aqueous phase was extracted with chloroform. The extracts and the oil were concentrated to dryness to obtain 11 g of the expected product.

| NMR (CDCl$_3$): | |
| --- | --- |
| 70 to 110 Hz | the 6H central CH$_2$'s |
| 132 Hz | N—CH$_3$ |
| 132 to 180 Hz | the 8H CH$_2$—N's |
| 73 Hz | the NH$_2$'s |

STEP C 4.8 g of 2,4-dichlorophenoxy acetic acid in solution in 15 ml of chloroform were added without exceeding 30° C. to a mixture of 1.6 g of 6-methyl-triaza-1,6,10-decane of Step B, 20 ml of chloroform and 2.02 g of triethylamind and after 3 hours of stirring at 20° C., the mixture was evaporated to dryness under reduced pressure. The residue was taken up in 180 ml of tetrahydrofuran and the insoluble part was filtered off. The filtrate was evaporated to dryness under reduced pressure and the 6.8 g of residue were chromatographed on silica (eluant: chloroform-methanol (9-1) to obtain 4 g of the expected product.

Analysis: $C_{24}H_{29}Cl_4N_3O_4$ Calculated: %C 50.98; %H 5.17; %Cl 25.09; %N 7.43; Found: %C 50.5; %H 5.0; %Cl 24.9; %N 7.4.

EXAMPLE 12

N-(1-naphthyl acetyl)-1,4-diamino butane and its hydrochloride

STEP A: 1-naphthyl-acetic acid chloride 15 g of 1-naphthyl acetic acid and 90 ml of thionyl chloride were heated with stirring for 2 hours and the solution was concentrated under reduced pressure. The residue was taken up in toluene and concentrated to dryness under reduced pressure to obtain 16.3 g of the expected product which used as is for the next step.

STEP B: N-(tert-butoxycarbonyl)-N'-(1-naphthyl acetyl)-1,4-diamino-butane

A solution of 16.3 g of 1-naphthyl-acetic acid chloride in 80 ml of chloroform was added at +10° C. to a solution cooled to +10° C. of 15 g of N-(tert-butoxycarbonyl)-1,4-diamino butane, 100 ml of chloroform and 14 ml of triethylamine and after one hour of stirring at ambient temperature, the mixture was concentrated to dryness under reduced pressure. The residue was taken up in water, separated and dried under reduced pressure at 50° C. to obtain 27.8 g of the expected product.

STEP C: N-(1-naphthyl-acetyl)-1,4-diamino-butane and its hydrochloride a) Preparation of the hydrochloride:

86 ml of 2N hydrochloric ethanol were added to a mixture of 27.76 g of the product of Step B and 200 ml of ethanol and was refluxed with stirring for one hour. The mixture was concentrated to dryness under reduced pressure to obtain 23.4 g of intermediate hydrochloride melting at ~130° C. after crystallization from ethyl acetate.

b) Obtaining the amine:

The 23.4 g of intermediate hydrochloride were taken up in 200 ml of water and 80 ml of N sodium hydroxide were added with stirring over 10 minutes at ambient temperature. Extraction was done with methylene chloride and the extracts were dried, filtered and evaporated to dryness under reduced pressure to obtain 19.08 g of crude product melting at <50° C. which was chromatographed on silica (eluant: methanol-ammonia (98-2)). The product obtained was triturated in ethyl acetate, then in ether to obtain 15.87 g of the expected product melting at 96° C.

Analysis: $C_{16}H_{20}N_2O$ (hydrated at 0.8%) Calculated: %C 74.97; %H 7.86; %N 10.93; Found: %C 74.0; %H 7.9; %N 10.7.

EXAMPLE 13

1-(1-naphthyl-acetyl)-triaza-1,6,10-decane dichlorhydride

STEP A:
1-(1-naphthyl-acetyl)-10-(tert-butoxycarbonyl)-triaza-1,6,10-decane 8.1 g of 3-[(tert-butoxycarbonyl)-amino]-1-bromopropane in solution in 40 ml of tert-butanol were added at reflux to a solution of 8.8 g of the product obtained in Step C of Example 12 in 50 ml of tert-butanol and 4.7 g of potassium carbonate. The mixture was refluxed with stirring for 3 hours 30 minutes and for 16 hours at ambient temperature. The insoluble part was filtered off, and the filtrate was concentrated under reduced pressure. The 17.21 g of residue were chromatographed on silica (eluant: methanol) to obtain 6.16 g of expected product.

STEP B: 1-(1-naphthyl acetyl)-triaza-1,6,10-decane dihydrochloride 5.9 g of the product of Step A, 60 ml of ethanol and 26 ml of 2N hydrochloric ethanol were refluxed with stirring for 2 hours 30 minutes and the mixture was separated. The product was triturated in ethyl acetate and then isopropyl ether to obtain 4.78 g of the expected product melting at 218° C.

Analysis: $C_{19}H_{29}Cl_2N_3O$ Calculated: %C 59.06; %H 7.57; %Cl 18.35; %N 10.88; Found: %C 58.8; %H 7.6; %Cl 18.3; %N 10.7.

EXAMPLE 14

N-(naphthoxy acetyl-1,4-diamino butane hydrochloride

STEP A: Naphthoxy acetic acid chloride 10 g of naphthoxy-acetic acid and 60 ml of thionyl chloride were refluxed for 2 hours and after evaporating to dryness under reduced pressure, several distillations with benzene were carried out to obtain 11.16 g of the expected product which was used as is for Step B.

STEP B: N'-(tert-butoxycarbonyl)-N-(2-naphthyl-acetyl)-1,4-diamino-butane 11.16 g of naphthoxy acetic acid chloride in solution in 50 ml of tetrahydrofuran were added at 0° C. to +10° C. to a solution of 10.32 g of N-(tert-butoxycarbonyl)-1,4-diamino butane in 110 ml of tetrahydrofuran and 6.7 g of triethylamine. The mixture was stirred for 90 minutes at ambient temperature and the insoluble part was filtered off. The fitrate was evaporated to dryness and the 17.78 g of residue were chromatographed on silica (eluant: hexane-ethyl acetate (1-1)) to obtain 10 g of the expected product melting at 102° C.

STEP C: N-(naphthoxy-acetyl)-1,4-diamino-butane hydrochloride 7.66 g of the product of Step B, 80 ml of ethanol and 14.7 ml of 2N hydrochloric ethanol were refluxed with stirring for 90 minutes and the mixture was cooled slowly, separated and dried to obtain 4.56 g of the expected product melting at 208° C.

Analysis: $C_{16}H_{20}N_2O_2$, HCl Calculated: %C 62.23; %H 6.85; %N 9.07; %Cl 11.48; Found: %C 62.2; %H 6.9; %N 9.0; %Cl 11.3.

EXAMPLE 15

1-(2-naphthoxy acetyl)-triaza-1,6,10-decane dichlorohydride

STEP A: N-(2-naphthoxy-acetyl)-1,4-diamino-butane

A mixture of 10.32 g of the product of Example 14, 200 ml of ethanol and 3.37 g of sodium bicarbonate was refluxed with stirring for 4 hours and after evaporating this mixture to dryness, the residue was crystallized from isopropyl ether to obtain 10 g of the expected product melting at 58° C.

STEP B: 1-(2-naphthoxy acetyl)-10-(tert.butoxycarbonyl)-triaza-1,6,10-decane dichlorohydride 4.37 g of 3-[(tert-butoxycarbonyl)-amino]-1-bromopropane and 20 ml of tert-butanol were added to a stirred refluxing mixture of 5 g of N-(2-naphthoxy-acetyl)-1,4-diamino-butane, 20 ml of tert-butanol and 2.54 g of potassium carbonate. The mixture was refluxed with stirring for 3 hours 30 minutes and for 16 hours at ambient temperature and the insoluble part was filtered off. The filtrate was evaporated under vacuum, and the residue was chromatographed on silica (eluant: methanol with 0.5% ammonia) to obtain 2.9 g of the expected product.

STEP C: 1-(2-naphthoxy-acetyl)-1,6,10-decan dichlorhydride 2.823 g of the product of Step B, 14 ml of ethanol and 8.5 ml of 2N hydrochloric ethanol were refluxed with stirring for 2 hours and the mixture was separated under argon and dried under reduced pressure to obtain 2 g of the expected product melting at 260° C.

Analysis: $C_{13}H_{27}N_3O_2 \cdot 2HCl$
Calculated: %C 56.71; %H 7.26; %N 10.44; %Cl 17.62;
Found; %C 56.5; %H 7.2; %N 10.5; %Cl 17.5.

EXAMPLE 16

N-2-allyl-3-trifluoromethyl-phenoxy acetyl 1,4-diamino-butane and its hydrochloride

STEP A: 3-trifluoromethyl-phenoxy-allyl 35.2 g of potassium carbonate wee added to 30 ml of 3-trifluoromethyl phenol in 50 ml of methyl ethyl ketone and the mixture was refluxed for one hour, then allowed to return to ambient temperature. 26 ml of allyl bromide in 10 ml of methyl ethyl ketone were added and after stirring for one hour and heating at reflux for 90 minutes, the mixture was allowed to return to ambient temperature and was stirred for 16 hours. Extraction was done with methylene chloride and the extracts were dried and concentrated to obtain 51.5 g of crude product which was taken up in water, alkalized with N sodium hydroxide and extracted with methylene chloride. The extracts were dried and concentrated to dryness to obtain 48.21 g of the expected product.

STEP B: 2-allyl-5-trifluoromethyl phenol and corresponding 3-trifluoromethyl isomer 29.7 g of the product of Step A were refluxed for 20 hours, then allowed to return to ambient temperature. After chromatography on silica (eluant: n-hexane-ethyl acetate 9-1), 8.79 g of product were recovered with a Rf=0.32 (isomer A 5—$CF_3$) and 12.36 g of product with a Rf=0.25 (isomer B 3—$CF_3$).

STEP C: Ethyl 2-allyl-3-trifluoromethyl-phenoxy-acetate 5.8 g of potassium carbonate were added to 6 g of the 3—$CF_3$ product of Step B in 30 ml of methyl ethyl ketone and the mixture was refluxed for one hour. It was allowed to return to ambient temperature and 3.7 ml of ethyl bromo-acetate were added, followed by reflux for one hour. The mixture was poured into water and extracted with methylene chloride. The extracts were dried and concentrated under reduced pressure. The crude product was taken up in water, alkalized with N sodium hydroxide and extracted with methylene chloride. The extract was dried, and the solvent was evaporated to obtain 8.17 g of the expected product.

STEP D: 2-allyl-3-trifluoromethyl-phenoxy-acetic acid 8.1 g of the product of Step C in 50 ml of ethanol was stirred for one hour at ambient temperature in the presence of 14 ml of 2N sodium hydroxide and 14 ml of 2N hydrochloric acid were then added with stirring for 15 minutes, followed by concentration to obtain 10.19 g of crude product which was taken up in water. After extracting with methylene chloride and drying, the solvent was evaporated to obtain 7.26 g of the expected product.

STEP E: 2-allyl-3-trifluoromethyl-phenoxy-acetic acid chloride 7 g of the product of Step D in 50 ml of thionyl chloride was refluxed for 2 hours and after concentrating, the residue was taken up in toluene. The solvents were eliminated under reduced pressure and the crude product obtained was used as is for Step F.

STEP F: N-(tert-butoxycarbonyl)-N'-[(2-allyl-3-trifluoromethyl)-phenoxy-acetyl]-diamino-1,4-butane Using the procedure of Example 1, 4.99 g of N-(tert-butoxycarbonyl)-1,4-diamino-butane and 7.40 g of (2-allyl-3-trifluoromethyl)-phenoxy acetic acid chloride were reacted to obtain 8.83 g of the expected product.

STEP G: N-2-allyl-3-trifluoromethyl-phenoxy-acetyl-1,4-diaminobutano and its hydrochloride Using the procedure of Example 1, 8.7 g of the product of Step F and 23 ml of about 2N hydrochloric acid in ethanol were reacted to obtain 8.52 g of hydrochloride which was alkalized with 23 ml of N sodium hydroxide to obtain 1.37 g of the expected product in the form of a base.

Analysis: $C_{16}H_{21}F_3N_2O_2$ solvated with 2% $H_2O$ Calculated: %C 58.17; %H 6.41; %F 17.25; %N 8.48; Found: %C 57.1; %H 6.4; %F 16.7; %N 8.3.

EXAMPLE 17

N-(2-allyl-5-trifluoromethyl-phenoxy acetyl)-diamino-1,4-butane and its hydrochloride

STEP A: Ethyl 2-allyl-5-trifluoromethyl-phenoxy-acetate

Using the procedure of Step C of Example 16, 5 g of the isomer A of Step B of Example 16 and 3.1 ml of ethyl bromoacetate were reacted to obtain 6.33 g of the expected product.

STEP B: 2-allyl-5-trifluoromethyl-phenoxy-acetic acid

Using the procedure of Step D of Example 16, 6.25 g of the product of Step A, 10.9 ml of 2N sodium hydroxide in 40 ml of ethanol were reacted and then 10.9 ml of 2N hydrochloric acid were added to obtain 5.28 g of the expected product.

STEP C: 2-allyl-5-trifluoromethyl-phenoxy-acetic acid chloride

Using the procedure of Step E of Example 16, 5.2 g of the product of Step B and 40 ml of thionyl chloride were reacted to obtain 5.55 g of the expected product which was used as is for Step D.

STEP D: N-tert-butoxycarbonyl-N'-[2-allyl-5-trifluoromethyl-phenoxy-acetyl]-diamino-1,4-butane Using the procedure of Example 1, 3.71 g of N-(tert-butoxycarbonyl)-1,4-diamino-butane and 5.5 g of (2-allyl-5-trifluoromethyl)-phenoxy acetic acid chloride were reacted to obtain 8.36 g of the expected product.

STEP E: N-(2-allyl-5-trifluoromethyl-phenoxy-acetyl)diamino-1,4-butane and its hydrochloride Using the procedure of Example 1, 8.20 g of the product of Step D and 21.1 ml of about 2N hydrochloric acid in ethanol were reacted to obtain 3.56 g of the hydrochloride which was alkalized with 9.7 ml of N sodium hydroxide. After extraction with methylene chloride, the organic phase was concentrated and the residue was chromatographed on silica (eluant: methanol-ammonia 98-2) to obtain 2.17 g of the expected product in the form of a base.

Analysis: $C_{16}H_{21}F_3N_2O_2$ solvated with 2% $H_2O$ Calculated: %C 58.17; %H 6.41; %F 17.25; %N 8.48; Found: %C 56.8; %H 6.4; %F 16.6; %N 8.1.

EXAMPLE 18

N-[6-(sec-butyl)-2,4-dichlorophenoxy]-acetyl-5-(guanidine)amino-pentane

STEP A: 3-benzyloxycarbonyl-1,3-thiazolidine-2-thione 12.9 ml of triethylamine cooled to 0° to 5° C. were added to 10 g of mercapto-thiazoline in solution in 200 ml of methylene chloride, then 12 ml of benzyl chloroformate in solution in 60 ml of methylene chloride were added dropwise. After stirring for 3 hours at ambient temperature, the mixture was poured into an iced solution of N hydrochloric acid and the aqueous phase was extracted with methylene chloride. The organic phase was dried and concentrated to dryness and the residue was chromatographed on silica (eluant: hexane-ethyl acetate 7-3) to obtain 17.9 g of the expected product melting at 72° C.

STEP B: N-benzyloxycarbonyl-1,5-diamino-pentane 17.84 g of the product of Step A in solution in 100 ml of methylene chloride were added to 16.4 g of 1,5-diamino-pentane in solution in 85 ml of methylene chloride and after stirring for 3 hours and concentration to dryness, the residue was chromatographed (eluant: methanol-ammonia 99-1) to obtain 10.5 g of the expected product.

STEP C: N-benzyloxycarbonyl-5-[(ditertbutoxycarbonyl)-guanidine)-amino-pentane 10.5 g of the product of Step B and 14.2 g of N,N'-bis(tert-butoxycarbonyl) S-methyl-thioisourea in 75 ml of tetrahydrofuran and 5 ml of water were refluxed for 3 hours and the mixture was cooled and poured over an aqueous solution of sodium bicarbonate. The mixture was extracted with methylene chloride and the organic phase was washed with water, dried and concentrated to dryness under reduced pressure. The residue was chromatographed on silica (eluant: hexane-ethyl acetate 7-3) to obtain 10 g of the expected product.

STEP D: 5-[(ditert-butoxycarbonyl)-guanidine]-amino-pentane 10 g of the product of Step C in ethanol was hydrogenated in the presence of 1 g of active charcoal with 10% palladium and the catalyst was filtered off. The filtrate was concentrated to dryness to obtain 6.74 g of the expected product.

STEP E:
N-[6-(sec-butyl)-2,4-dichlorophenoxy]-acetyl-5-[(ditert-butoxycarbonyl)-guanidine]-amino-pentane Using the procedure of Step E of Example 7, 6 g of 5-(ditert-butoxycarbonyl-guanidine)-amino-pentane and 5.5 g of the product of Step D of Example 6 were reacted and after chromatography on silica (eluant: methylene chloride), 6.52 g of the expected product were obtained.

STEP F:
N-[6-(sec-butyl)-2,4-dichlorophenoxy]-acetyl-5-guanidine)-amino-pentane 7 ml of an ethanol solution of 3.3N hydrochloric acid were added to 6.52 g of the product of Step E in solution in 65 ml of ethanol and the mixture was refluxed for 24 hours. After cooling to ambient temperature and concentrating to dryness under reduced pressure, the residue was taken up in water and extracted with ethyl acetate to obtain 3.55 g of the expected product.

Analysis: $C_{18}H_{29}Cl_3N_4O_2$ Calculated: %C 49.2; %H 6.6; %Cl 24.2; %N 12.7; Found: %C 49.1; %H 6.7; %Cl 24.3; %N 12.8.

EXAMPLE 19

Using the procedure of Step E of Example 7, starting with 1.68 g of the amine obtained as indicated in preparation 2 and 3.4 of product obtained as in Step E of Example 6, 3.7 g of expected product is obtained.

STEP B:
N-[6-(sec-butyl)-2,4-dichlorophenoxy]-acetyl-diamino-1,3-propane hydrochloride Using the procedure of Step F of Example 18, starting with 3.69 g of the product prepared in Step A and 2.9 ml of 3.3N hydrochloric acid, 3.05 g of expected product were obtained.

Analysis: $C_{15}H_{23}Cl_3N_2O_2$ Calculated: %C 48.7; %N 6.3; %Cl 28.8; %N 7.6; Found: %C 48.2; %N 6.4; %Cl 28.8; %N 7.3.

EXAMPLE 20

N-[6-(sec-butyl)-2,4-dichlorophenoxy]-acetyl-3-guanidineamino-propane hydrochloride

STEP A:
N-[6-(sec-butyl)-2,4-dichlorophenoxy]-acetyl-3-[(ditert-butoxycarbonyl)]-guanidine-amine-propane 1.1 g of sodium bicarbonate were added to 3.93 g of N-[6-(sec-butyl-2,4-dichlorophenoxy)-acetyl]-1,3-diaminopropane hydrochloride of Example 19 in solution in 50 ml of ethanol and the mixture was refluxed for 4 hours 30 minutes, then left for 12 hours at ambient temperature. After concentration to dryness, dilution with water and extraction with methylene chloride, the organic phase was concentrated to dryness to obtain 3.47 g of amine which was added to 3.63 g of N,N'-bis-(tert-butoxycarbony)-S-methyl-thioisourea in 20 ml of tetrahydrofuran and 20 ml of water. The mixture was refluxed for 3 hours 30 minutes, cooled to ambient temperature, and poured into a 10% aqueous solution of sodium bicarbonate. After extraction with methylene chloride, the combined organic phases were dried and concentrated to dryness under reduced pressure. After chromatography on silica (eluant: hexane-ethyl acetate 75-25), 2.4 g of the expected product were obtained.

STEP B: N-[6-(sec-butyl)-2,4-dichlorophenoxy]-acetyl-3-guanidine-amino-propane hydrochloride Using the procedure of Step F of Example 18, 2.4 g of the product of Step A were reacted to obtain 1.42 g of the expected hydrochloride.

IR Spectrum ($CHCl_3$):
NH: 3418-3335-3165 cm$^{-1}$
C=O: 1669 cm$^{-1}$
C=C, C=N, CONH, amide II: 1620-1583-1565-1542 cm$^{-1}$

EXAMPLE 21

N-[6-(sec-butyl)-2,4-dichlorophenoxy]-acetyl-diamino-1,5-pentane hydrochloride

STEP A:
N'-[6-(sec-butyl)-2,4-dichlorophenoxy]-acetyl-N-tert-butoxy-carbonyl-diamino-1,5-pentane Using the procedure of Step E of Example 7, 1.9 g of the amine and 3.32 g of the product of Step B of Example 6 were reacted to obtain 3.92 g of the expected product.

STEP B:
N-[6-(sec-butyl)-2,4-dichlorophenoxy]-acetyl-diamino-1,5-pentane hydrochloride Using the procedure of Step F of Example 18, 3.88 g of the product of Step A and 3 ml of 3.3N hydrochloric acid were reacted to obtain 2.88 g of the expected product.

IR Spectrum ($CHCl_3$):
NH: 3425 cm$^{-1}$
C=O: 1673 cm$^{-1}$
C=C, aromatic, CO amide II: 1610-1584-1565-1538 cm$^{-1}$

EXAMPLE 22

N-[6-(sec-butyl)-2,4-dichlorophenoxy]-acetyl-4-guanidine-aminobutane hydrochloride Using the procedure of Step F of Example 18, 4.49 g of the product of Step B of Example 7 and 5 ml of 3.3N hydrochloric acid were reacted to obtain the hydrochloride which was diluted in methylene chloride, dried and concentrated to dryness. After crystallization from isopropyl ether, 2.4 g of the expected product were obtained.

EXAMPLE 23

(2-sec-butyl-5-trifluoromethyl-phenoxyacetyl)-triaza-1,6,10-decane dihydrochloride

STEP A: (3-trifluoromethylphenoxy)-2-butene 18 g of potassium carbonate were added to 15 ml of 3-trifluoromethylphenol and 25 ml of 2-butanone with stirring and then 15.1 ml of 2-bromobutene in 70 ml of 2-butanone were added. The mixture was refluxed for 90 minutes, then stirred for 72 hours at ambient temperature. 300 ml of water were then added, followed by extraction with methylene chloride. The extracts were dried and concentrated to dryness to obtain 21.73 g of the expected product.

STEP B:
5-trifluoromethyl-2-(1-methyl-2-propenyl)-phenol 123.3 g of product of Step A were refluxed for 2 hours and chromatographed on silica (eluant: n-hexane-diisopropyl ether 9-1, then 8-2) to obtain 16.95 g of the expected product.

STEP C: 5-trifluoromethyl-2-(1-methylpropyl)-phenol 4.59 g of the product of Step B in 200 ml of ethanol was hydrogenated in the presence of 0.50 g of active charcoal with 10% palladium and after filtering, the filtrate was concentrated to obtain 4.05 g of the expected product.

STEP D: Ethyl [5-trifluoromethyl-2-(1-methylpropyl)-phenoxy]-acetate 2.5 ml of ethyl bromoacetate were added to 4 g of the product of Step C in 15 ml of dimethylsulfoxide and 4 g of potassium carbonate were added, followed by heating at 80° C. for 2 hours 30 minutes. The reaction medium was poured into iced water and extracted with methylene chloride. The extracts were dried and concentrated to dryness to obtain 5.10 g of the expected product.

STEP E: [5-trifluoromethyl-2-(1-methylpropyl)]-acetic acid 3 g of the product of Step D and 8 ml of 2N sodium hydroxide in 10 ml of ethanol were stirred for 45 minutes at ambient temperature and after concentration, and then dilution with water, followed by extraction with methylene chloride, the mixture was acidified to pH=1 and extracted with ethyl acetate. The extracts were washed with water and dried, and the solvents were eliminated under reduced pressure. After washing with hexane, 1.24 g of the expected product melting at 96° C. were obtained.

STEP F: N-(2-sec-butyl-5-trifluoromethyl-phenoxyacetyl)-10-tert-butoxycarbonyl-triaza-1,6,10-decane 3 g of [5-trifluoromethyl-2-(2-butyl)-phenoxy]-acetic acid in 30 ml of methylene chloride were cooled to 0° to +5° C. in the presence of 1.44 g of 2-mercapto-thiazoline and 0.30 g of 4-dimethylamino-pyridine and 2.47 g of dicyclohexylcarbodiimide in solution in 20 ml of methylene chloride were progressively added. The mixture was stirred for one hour at 0° C., then for 16 hours at ambient temperature and after filtering the filtrate was concentrated to dryness to obtain 5.46 g of residue. The latter was chromatographed on silica (eluant: methylene chloride) to obtain 2.70 g of the product which was dissolved in 30 ml of methylene chloride. 1.8 g of the product of Step D of Example 8 in solution in 20 ml of methylene chloride were added. The mixture was stirred for 16 hours at ambient temperature and concentrated to dryness. The residue was chromatographed on silica (eluant: methanol) to obtain 2.62 g of the expected product.

STEP G: (2-sec-butyl-5-trifluoromethyl phenoxy acetyl)-triaza-1,6,10-decane dihydrochloride 1.48 g of the product of Step F in 20 ml of a methanol solution of 2N hydrochloric acid was refluxed for 3 hours, concentrated under reduced pressure and dried under reduced pressure to obtain 1.21 g of the expected product.

Analysis: $C_{20}H_{34}Cl_2F_3N_3O_2$ Calculated: %C 50.42; %H 7.19; %Cl 14.88; %F 11.96; %N 8.82; Found: %C 50.4; %H 7.6; %Cl 14.8; %F 10.8; %N 8.0.

EXAMPLE 24

N-(3-methoxy-4-hydroxyphenoxy-acetyl)-diamino-1,4-butane and its hydrochloride

STEP A: 4-benzyloxy-3-methoxyphenol 24.2 g of 4-benzyloxy-3-methoxy benzaldehyde (Beilst. Vol. 8, II p 283) were dissolved in 100 ml of acetic acid and a mixture of 25 ml of peracetic acid and 50 ml of acetic acid was added without exceeding 45° C. The mixture was stirred for 18 hours at +40° C. and after concentration to dryness, the residue was chromatographed on silica (eluant: hexane-ethyl acetate 8-2) to obtain 9.1 g of the expected product melting at 84° C.

STEP B: Ethyl 4-benzyloxy-3-methoxyphenoxy-acetate

Using the procedure of Step C of Example 16, 2.76 g of the product of Step A, 1.82 g of potassium carbonate, 15 ml of methyl ethyl ketone and 1.6 ml of ethyl bromoacetate were reacted. Extraction was carried out with methyl ethyl ketone and the organic phase was concentrated to dryness to obtain 3.9 g of crude product which was chromatographed on silica (eluant: hexane-ethyl acetate 8-2) to obtain 3.6 g of the expected product melting at 58° C.

STEP C: 4-benzyloxy-3-methoxyphenoxy-acetic acid

Using the procedure of Step D of Example 16, 3.2 g of the product of Step B and 5 ml of 2N sodium hydroxide and then 5 ml of hydrochloric acid were reacted to obtain 2.85 g of the expected product.

STEP D: N-(3-methoxy-4-benzyloxy-phenoxy-acetyl)-N-tert-butoxycarbonyl-diamino-1,4-butane Using the procedure of Step F of Example 23, 2.8 g of 4-benzyloxy-methoxyphenoxy-acetic acid, 115 mg of 4-dimethylamino-pyridine, 2 g of dicyclohexylcarbodiimide and 1.8 g of N-tert-butoxycarbonyl-diamino-1,4-butane were reacted and after chromatography on silica (eluant: chloroform-acetone-cyclohexane 1-1-2), 2.4 g of the expected product were obtained.

STEP E: N-(3-methoxy-4-hydroxyphenoxy acetyl)-N'-tert-butoxycarbonyldiamino-1,4-butane 2.4 g of the product of Step D in 100 ml of ethanol with 50 ml of cyclohexane were hydrogenated in the presence of 2.4 g of active charcoal with 10% palladium and were then refluxed for 3 hours, followed by cooling, filtering and concentrating the filtrate to dryness to obtain 1.96 g of the expected product.

STEP F: N-(3-methoxy-4-hydroxyphenoxy-acetyl)-diamino-1,4-butane and its hydrochloride Using the procedure of Step G of Example 1, 1.96 g of the product of Step E were reacted to obtain 1.56 g of hydrochloride. Then, 1.28 g of the expected base were obtained after chromatography on silica (eluant: methanol-ammonia 98-2) which melted at 100° C.

IR Spectrum (CHCl$_3$):
OH-NH: 3303 cm$^{-1}$
C=O: 1652 cm$^{-1}$
NH$_2$, aromatic, amide II: 1612-1574-1545-1491 cm$^{-1}$

EXAMPLE 25

N-(2,4-dichlorophenoxy acetyl)-N'-[1-(3-indol-acetyl)]-diamino-1,4-butane

Using the procedure of Example 23, Step A, 2 g of 3-indolyl-acetic acid, 0.135 g of 4-dimethylamino-pyridine, 2.35 g of dicyclohexylcarbodiimide and 3.32 g of N-(2,4-dichlorophenoxy-acetyl)-diamino-1,4-butane were reacted and after chromatography on silica (eluant: hexane-ethyl acetate 6-4, then methanol), 3.4 g of the expected product melted at 128° C. were obtained.

EXAMPLE 26

N-(7-hydroxy-coumarinyl-4-acetyl)-diamino-1,4-butane

STEP A: 7-hydroxy-coumarin-4-acetic acid 84 g of citric acid and 112 ml of concentrated sulfuric acid were stirred for one hour at ambient temperature and then heated progressively to 70° C. and maintained there for 35 minutes. The mixture was cooled to 0° C. and 34.56 g of 1,3-benzene diol and 44.8 ml of concentrated sulfuric acid were added. The mixture was maintained for 16 hours at 0° C. and then poured over ice. The crystallized product was separated off and dried under reduced pressure to obtain after crystallization from water, 22.77 g of the expected product melting at 210° C.

STEP B:
N-tert-butoxycarbonyl-N'-(7-hydroxy-coumarinyl-4-acetyl)-diamino-1,4-butane 8.9 g of 7-hydroxy-coumarin-4-acetic acid in 135 ml of tetrahydrofuran were added to a suspension of 12.64 g of 2-chloro-N-methyl pyridinium iodide in 135 ml of tetrahydrofuran and then 7.52 g of N-tert-butoxycarbonyl-diamino-1,4-butane 1 in 100 ml of tetrahydrofuran were added. Then, 13.5 ml of triethylamine were added, and the mixture was refluxed for 6 hours. The mixture was stirred for 16 hours at ambient temperature and after filtering, the filtrate was concentrated. The residue was taken up in water and the crystals were dried and purified by chromatography on silica (eluant: ethyl acetate-n-hexane 8-2) to obtain 4.46 g of the expected product melting at 171° C.

STEP C:
N-(7-hydroxy-coumarinyl-4-acetyl)-diamino-1,4-butane hydrochloride

Using the procedure of Example 8, Step F, 4.32 g of the product of Step A and 7.5 ml of 2.2N hydrochloric acid were reacted to obtain 2.67 g of the expected product which after crystallization from methanol melted at 220° C.

Analysis: $C_{15}H_{19}ClN_2O_4$ Calculated: %C 55.13; %H 5.86; %Cl 10.85; %N 8.57; Found: %C 54.9; %H 5.9; %Cl 11.2; %N 8.4.

EXAMPLE 27

N-[(2-methyl-6-indolyloxy)-acetyl]-1,4-diamino-butane hydrochloride

STEP A:
N-(tert-butoxycarbonyl)-N'-[(2-methyl-6-indolyloxy)-acetyl]-1,4-diamino-butane 1.07 g of sodium hydride in suspension in 50% of oil were added progressively to a solution of 3.28 g of 6-hydroxy-2-methyl indole in 50 ml of dimethylformamide and the suspension was stirred for one hour. A solution of 6.5 g of N'-(tertbutoxycarbonyl)-N-(chloroacetyl)-1,4-diamino-butane and 60 ml of dimethylformamide was slowly introduced. The reaction medium was stirred at 90° C. for 5 hours, then for 16 hours at ambient temperature. The suspension obtained was evaporated to dryness to obtain 13.08 g of a product which was chromatographed on silica and eluted with a hexane-ethyl acetate mixture (30-70) to obtain 4.98 g of the sought product melting at 132° C.

STEP B:
N-[(2-methyl-6-indolyloxy)-acetyl]-1,4-diamino-butane hydrochloride 9.9 ml of a 2N hydrochloric acid solution in ethanol were added to a suspension of 4.96 g of the product of Step A in 50 ml of ethanol and the reaction mixture was refluxed with stirring for one hour. The solution was evaporated to dryness and the 5.70 g of crude product were taken up in 20 ml of acetonitrile. 3 ml of propylene oxide were added and the reaction mixture was stirred for 30 minutes. The reaction mixture was concentrated and the product was triturated in isopropyl ether, separated and dried to obtain 3.88 g of the sought product melting at 129° C.

EXAMPLE 28

N-(3-trifluoromethyl-phenoxy acetyl)-N-[1-(2-trifluoromethyl-3-indolacetyl)]-diamino-1,4-butane

STEP A: Ethyl 5,5,5-trifluoro-4-oxo-3-ethoxycarbonyl-pentanoate 200 g of diethyl succinate and 82 g of ethyl trifluoroacetate were mixed together and 13.2 g of sodium and 200 ml of ether were added over 5 minutes. The reaction medium was heated for 18 hours at 80° C., and then poured into 200 ml of iced 10N sulfuric acid. After decanting, drying and concentrating, the expected product was obtained which was used as is for the following step.

STEP B: Ethyl 5,5,5-trifluoro-4-oxo-pentanoate 45 g of the product of Step A, 10.3 g of boric acid and 1 g of p-toluenesulfonic acid were heated at 180° C. for 3 hours and the mixture was poured into ice and extracted with ethyl acetate. The mixture was decanted, dried and concentrated under reduced pressure and the residue was distilled to obtain 10.8 g of expected product.

STEP C: Ethyl 3-(2-trifluoromethylindolyl)-acetate

A solution of 5.9 g of phenyl hydrazine in 10 ml of ethanol was added to 10.8 g of product of Step B in solution in 15 ml of ethanol and then 2.74 ml of 2N hydrochloric acid in solution in ethanol were added. The mixture was stirred for 3 hours at 20° C. and then concentrated under reduced pressure to obtain 17.6 g of intermediate which was taken up in 50 ml of ethanol, cooled to +4° C. and treated with a gaseous current of hydrochloric acid. After heating for 24 hours at reflux, then filtering, the filtrate was concentrated. The residue was chromatographed on silica (eluant: cyclohexane-isopropyl ether 7-3) to obtain 6.9 g of the expected product melting at 86° C.

STEP D: 3-(2-trifluoromethylindolyl)-acetic acid 2.15 g of sodium bicarbonate were added in three lots to a solution of 3.08 g of the product of Step C in 20 ml of methanol and 10 ml of water followed with stirring for 24 hours. The solution was concentrated and the residue was taken up with 20 ml of water, acidified with hydrochloric acid and extracted with ethyl acetate. The organic phase was dried and concentrated to dryness. The residue was chromatographed on silica (eluant: hexane-ethyl acetate-acetic acid 78-20-2) to obtain 2.6 g of the expected product melting at 146° C.

STEP E

Using the procedure of Step B of Example 26, 6.01 g of 2-chloro-N-methyl pyridinium iodide, 4.77 g of 3-(2-trifluoromethyl indolyl)-acetic acid, 5.51 g of N-(3-trifluoromethylphenoxy acetyl)-1,4-diamino-butane obtained from the hydrochloride of Example 4 and 6.55 ml of triethylamine were reacted to obtain after chromatography on silica (eluant: ethyl acetate), 4.85 g of expected product.

Analysis: $C_{11}H_{18}F_3NO_2$ Calculated: %C 54.32; %H 3.31; %F 23.43; %N 5.76; Found: %C 54.40; %H 3.3; %F 23.1; %N 5.5.

EXAMPLE 29

1,10-(3-indolacetyl)-1,6,10-triazadecane

Using the above procedure, the appropriate acid and amine were reacted to obtain the expected product.

Analysis: $C_{27}H_{33}N_5O_2$ Calculated: %C 70.55; %H 7.23; %N 15.21; Found: %C 70.3; %H 7.4; %N 15.0.

Preparation 1: N-(tert-butoxycarbonyl)-1,4-diamino butane 400 g of di-tert-butoxycarbonyl in solution in 2000 ml of methylene chloride were added over one hour at 0° C. to +5° C. to a solution of 320 g of 1,4-diamino-butane in 2800 ml of methylene chloride and after stirring for one hour at 20° C., the insoluble part was filtered off. The filtrate was evaporated to dryness under reduced pressure and the 363.1 g of oil obtained were chromatographed on silica (eluant: flugene (113)-methanol (9-1), then methanol, then methanol-ammonia (96-4)) to obtain 203.6 g of expected product.

| NMR Spectrum (CDCl$_3$): |
| --- |
| tBu ~ 87 Hz |
| C$\underline{H}_2$ NH$_2$ ~ 162 Hz |
| C$\underline{H}_2$ NHCO ~ 186 Hz |
| C = 0 ~ 280 Hz |
| CH$_2$ (central) ~ 89 Hz |

Preparation 2: N-(tert-butoxycarbonyl)-1,3-diamino-propane

A solution of 46 g of di-tert-butyl-carbonate in 120 ml of methylene chloride was added at +5° C. without exceeding +10° C. to a solution of 36 ml of 1,3-diamino-propane in 160 ml of methylene chloride and after stirring for 16 hours at 20° C., the insoluble part was filtered off. The filtrate was evaporated to dryness under vacuum to obtain 63 g of residue which was chromatographed on silica (eluant: methanol with 2% ammonia) to obtain 23 g of the expected product melting at <60° C.

Preparation 3: 3-[(tert-butoxycarbonyl)-amino]-1-bromo-propane

STEP A: 3-[(tert-butoxycarbonyl)-amino]-1-propanol 21.8 g of di-tert-butyl-dicarbonate in solution in 50 ml of tetrahydrofuran were added at ambient temperature to a solution of 7.5 g of 3-amino-2-propanol in 75 ml of water and 75 ml of tetrahydrofuran. After 2 hours of stirring at 20° C., then evaporation to dryness under reduced pressure, the oily residue was taken up in 150 ml of ethyl acetate. The solution was washed twice with 30 ml of 0.5M acetic acid, then with water, and evaporated to dryness under vacuum to obtain 15.4 g of the expected product.

STEP B:

3-[(tert-butoxycarbonyl)-amino]-1-bromopropane 25 g of carbon tetrabromide in solution in 50 ml of acetonitrile were slowly added at a temperature between 20° and 25° C. to a solution of 9 g of the product of Step A in 120 ml of tetrahydrofuran and 19.7 g of triphenyl phosphine. After stirring for 15 hours, the insoluble part was filtered off and the filtrate was concentrated to dryness under reduced pressure. The 45 g of residue were chromatographed on silica (eluant: hexane-ethyl acetate (8-2)) to obtain 9.4 g of the expected product melting at 40° C.

| IR spectrum (CHCl$_3$): | |
| --- | --- |
| =C—NH | 3460 cm$^{-1}$ |
| CO (carbamate) | 1708 cm$^{-1}$ |
| secondary amide | 1505 cm$^{-1}$ |
| Me t.Bu | 1368 cm$^{-1}$ |

Preparation 4: N-tert-butoxycarbonyl-diamino-1,5-pentane 54 ml of 1,5-diamino-pentane in 200 ml of methylene chloride were cooled to +5° C. and then 50 g of di-tert-butyl dicarbonate in solution in methylene chloride were added. The mixture was stirred for 15 minutes at 0° C., allowed to return to ambient temperature and stirred for 16 hours. After filtering, the filtrate was concentrated to dryness and the 38 g of crude product was chromatographed on silica (eluant: methanol-ammonia 98-2) to obtain 18.31 g of the expected product.

BIOLOGICAL FUNGICIDE ACTIVITY

Description of the tests a) Inhibition of the germination of spores

The inhibiting activity on the germination was measured on spores of Alternaria solani and Fusarium roseum. The products were dissolved in "Napsol PM1" and each solution was diluted with 8 ml of hot "PDA" (0.9% of "Napsol PM1" in the final solution) in a Petri dish (50 mm diameter). Each product was tested at the concentration of: 100 or 1000 ppm. When the medium had gelled, the suspension of spores was deposited on the surface at 200 microliters per dish and the suspension contained 100,000 spores per ml. The germination was checked 18 hours after the seeding and the values set out in the table below give the percentage of inhibition of germinated spores in two dishes. "Napsol PM1": methyl ether of monopropylene glycol. "PDA": Agar glucosed with potato.

b) *Botrytis cinerea* tests on a vine

Young vine plants from cuttings (Grenache N variety, clone 70) were cultivated in a greenhouse (day temperature: 30° C., night temperature: 25° C.) in an earth/compost/sand mixture, (⅓-⅓-⅓). Two days before the test, the plants were transported into a culture chamber (same temperature conditions: humidity: 60% by day, 80% by night) and the product was dissolved in "matrix A" at a concentration of 500 ppm just before use. The treatment was effected by spraying the solution onto the leaves until retention was at a maximum. The Botrytis cinerea spores were suspended in diluted carrot juice at a rate of 50,000 spores per ml. The contamination was effected by depositing the spore suspension in the form of drops (20 microliters) on the abaxial surface of the leaves. In the preventative test, the treatment was carried out one day before contamination and in the curative test, the contamination was carried out two days before the treatment. The plants were then kept in the culture chamber under the same conditions as previously. Checks were made 9 days after contamination by measuring the necrosed surfaces and the effectiveness of the product was calculated relative to a non-treated control.

c) *Plasmopara viticola* tests

The vegetable material used was the same as that used in test B and cultivated under the same conditions and the treatment was also carried out in the same way. Contamination was effected with a suspension of zoosporangia of Plasmopara viticola taken immediately before the test (50,000 zoosporangia per ml). Drops of suspension (20 microliters) were deposited on the abaxial surface of the leaves. Next, the plants were kept 24 hours in an atmosphere with saturated humidity, then returned to the humidity of the culture chamber (60% by day, 80% by night). Checks were made 10 days after contamination by measuring the development of the islets of conidiophores on the abaxial surface of the leaves and the effectiveness of the product was calculated in relation to a non-treated control.

d) *Erysiphe graminis hordei* test

Barley seeds (Pression variety) were germinated in an earth/compost/sand mixture (⅓-⅓-⅓) and cultivated in a greenhouse. The products were dissolved in the "matrix A" just before the test at a concentration of 500 ppm and the treatment was carried out by spraying the product solution on the 10-day old barley plants until retention was maximum. The contamination by conidia of Erysiphe graminis hordei was effected 3 days after the treatment. The plants were kept in a climatized room (day temperature: 23° C., night temperature: 18° C.) and 7 days after contamination, the spread of conidian covering an the first and second leaf of each plant was measured. The effectiveness of the product was calculated relative to a non-treated control.

e) *Puccinia recondita tritici* tests

Wheat grains (Festival variety) were germinated in an earth/compost/sand mixture (⅓-⅓-⅓) and the plants were cultivated in a greenhouse. The products were dissolved in the "matrix A" just before the test at a concentration of 500 ppm and the treatment was carried out by spraying the product solution on the 9-day old wheat plants until retention was maximum. The contamination by uredospores of Puccinia recondita tritici was effected the day after the treatment and the plants were kept in an air-conditioned room (day temperature: 22° C., night temperature: 18° C.). 7 days after contamination, the density of spores on the first two leaves of each plant was measured and the effectiveness of the product was calculated relative to a non-treated control.

| Biological Properties | | | | |
|---|---|---|---|---|
| | Inhibition of the germination of the spores | | | |
| | ALT 100 | ALT 1000 | FUS 100 | FUS 1000 |
| Ex. 1 | — | 100 | 0 | 100 |
| Ex. 8 | 100 | 100 | 0 | 100 |
| Ex. 6 | 100 | 100 | 60 | 100 |
| Ex. 11 | — | 100 | — | 100 |
| Ex. 20 | 0 | 100 | 0 | 100 |
| Ex. 21 | 100 | 100 | 0 | 100 |
| Ex. 18 | 100 | 100 | 0 | 70 |
| Ex. 22 | 0 | 100 | 0 | 100 |
| Ex. 19 | 100 | 100 | 0 | 100 |

ALT = Altenaria solani, FUS = Fusarium roseum

| "in vivo" fungicide properties | | | | | |
|---|---|---|---|---|---|
| | BOT PRE | PLA PRE | PLA CUR | ERY PRE | PUC PRE |
| Ex. 1 | 70.00 | 100.00 | 90.00 | 50.00 | — |
| Ex. 3 | — | — | 90.00 | 60.00 | — |
| Ex. 5 | — | — | 80.00 | 20.00 | — |
| Ex. 12 | — | 90.00 | 50.00 | 50.00 | — |
| Ex. 8 | 80.00 | 100.00 | — | 80.00 | 10.00 |
| Ex. 6 | 80.00 | 90.00 | — | 60.00 | 50.00 |
| Ex. 7 | 40.00 | 100.00 | — | 60.00 | 20.00 |
| Ex. 20 | 80.00 | 100.00 | — | 20.00 | 50.00 |
| Ex. 21 | 70.00 | 100.00 | — | 30.00 | 30.00 |
| Ex. 18 | — | — | — | 10.00 | — |
| Ex. 22 | 80.00 | 100.00 | — | — | 60.00 |
| Ex. 19 | 40.00 | — | — | 30.00 | 30.00 |

| Examples of compositions of matrices | | |
|---|---|---|
| Matrix A: | SOLVESSO 150 | 70.0 g |
| | NAPSOL PM1 | 850.0 g |
| | SURFAROX HRH 40C | 52.0 g |
| | ECD 1604 | 28.0 g |
| | | 1000.0 g |
| Matrix B: | SOLVESSO 150 | 64.5 g |
| | NAPSOL PM1 | 183.0 g |
| | PROPANEDIOL 1.2 | 158.5 g |
| | SURFAROX HRH 40C | 104.0 g |
| | ECD 1604 | 54.5 g |
| | PERMUTED WATER | 435.5 g |
| | | 1000.0 g |

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula

$$R_1-CH_2-\overset{O}{\underset{\|}{C}}-NH-W-NH-Z \qquad I$$

wherein $R_1$ is Ar—O—, Ar is aryl of 6 to 14 carbon atoms unsubstituted or substituted, W is —$(CH_2)_{n1}$—, $n_1$ is an integer from 2 to 6, the substitutents being at least one substituent selected from the group consisting of hydroxyl, halogen, alkyl, alkenyl and alkynyl of up to 12 carbon atoms, aryl of 6 to 14 carbon atoms, —$CF_3$, —OR"₃ in which R"₃ is alkyl of 1 to 12 carbon atoms or arylalkyl of 7 to 18 carbon atoms, COalkyl, —Si(alkyl)₃, —SO₂alkyl in which the alkyl contains 1 to 12 carbon atoms, and —SO₂aryl in which the aryl contains 6 to 14 carbon atoms, the various groups being able between them to form, with the atoms to which they are linked, —O—CH₂—O— rings, Z is hydrogen or a non-toxic, pharmaceutically acceptable acid addition salt thereof.

2. A compound of claim 1 wherein the substituents on the aryl are selected from the group consisting of —OH, halogen, alkyl of 1 to 14 carbon atoms, alkenyl and alkynyl of 2 to 14 carbon atoms, —CF₃, —OR"₃, —COAlk, —Si(Alk)₃, —SO₂Alk, —SO₂Ar and —OCH₂—O—, R"₃ is alkyl of 1 to 12 carbon atoms or aralkyl of 7 to 18 carbon atoms, Alk is alkyl of 1 to 12 carbon atoms and Ar is aryl of 6 to 14 carbon atoms.

3. A compound of claim 1 wherein W is —(CH₂)₃— or —(CH₂)₄— or —(CH₂)₅—.

4. A compound of claim 1 wherein R₁ is

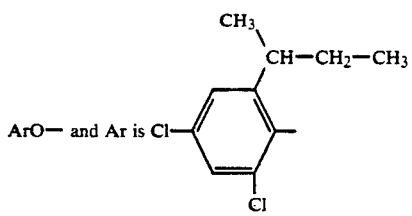

5. A compound of claim 1 selected from the group consisting of N-[(6-sec-butyl-2,4-dichloro-phenoxy)-acetyl]-diamino-1,4-butane, 3,3'-[N-(6-sec-butyl-2,4-dichlorophenoxy)-acetyl]-3,3'-diamino-dipropylamine, N-[(6-sec-butyl-2,4-dichlorophenoxy)-acetyl]-1,3-diamino-propane, N-[(6-sec-butyl-2,4-dichlorophenoxy)-acetyl]-1,5-diamino-pentane and their non-toxic, pharmaceutically acceptable acid addition salts.

6. A fungicidal composition comprising a fungicidally effective amount of at least one compound of claim 1 and an inert carrier.

7. A composition of claim 6 wherein the substituents on the aryl are selected from the group consisting of —OH, halogen, alkyl of 1 to 14 carbon atoms, alkenyl and alkynyl of 2 to 14 carbon atoms, —CF₃, —OR"₃, —COAlk, —Si(Alk)₃, —SO₂Alk, —SO₂Ar and —OCH₂—O—, R"₃ is alkyl of 1 to 12 carbon atoms or aralkyl of 7 to 18 carbon atoms, Alk is alkyl of 1 to 12 carbon atoms and Ar is aryl of 6 to 14 carbon atoms.

8. A composition of claim 6 wherein W is —(CH₂)₃— or (CH₂)₄— or —(CH₂)₅—.

9. A composition of claim 6 wherein R₁ is

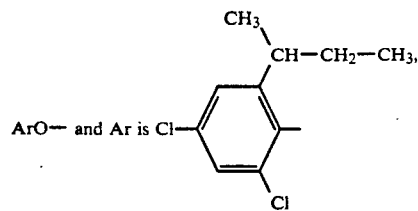

10. A composition of claim 6 wherein the active compound is selected from the group consisting of N-[(6-sec-butyl-2,4-dichloro-phenoxy)-acetyl]-diamino-1,4-butane, 3,3'-[N-(6-sec-butyl-2,4-dichlorophenoxy)-acetyl]-3,3'-diamino-dipropylamine, N-[(6-sec-butyl-2,4-dichlorophenoxy)-acetyl]-1,3-diamino-propane, N-[(6-sec-butyl-2,4-dichlorophenoxy)-acetyl]-1,5-diamino-pentane and their non-toxic, pharmacuetically acceptable acid addition salts.

11. A method of combatting fungi comprising contacting fungi with a fungicidally effective amount of at least one compound of claim 1.

12. A method of claim 11 wherein the substituents on the aryl are selected from the group consisting of —OH, halogen, alkyl of 1 to 14 carbon atoms, alkenyl and alkynyl of 2 to 14 carbon atoms, —CF₃, —OR"₃, —COAlk, —Si(Alk)₃, —SO₂Alk, —SO₂Ar and —OCH₂—O—, R"₃ is alkyl of 1 to 12 carbon atoms or aralkyl of 7 to 18 carbon atoms, Alk is alkyl of 1 to 12 carbon atoms and Ar is aryl of 6 to 14 carbon atoms.

13. A method of claim 11 wherein W is —(CH₂)₃— or (CH₂)₄— or —(CH₂)₅—.

14. A method of claim 11 wherein R₁ is

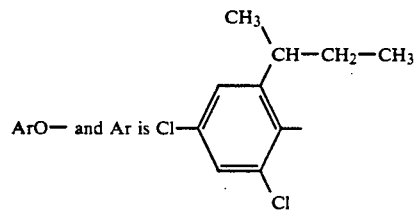

15. A method of claim 11 wherein the active compound is selected from the group consisting of N-[(6-sec-butyl-2,4-dichloro-phenoxy)-acetyl]-diamino-1,4-butane, 3,3'-[N-(6-sec-butyl-2,4-dichlorophenoxy)-acetyl]-3,3'-diamino-dipropylamine, N-[(6-sec-butyl-2,4-dichlorophenoxy)-acetyl]-1,3-diamino-propane, N-[(6-sec-butyl-2,4-dichlorophenoxy)-acetyl]-1,5-diamino-pentane and their non-toxic, pharmacuetically acceptable acid addition salts.

16. A compound of claim 1 wherein n₁ is an integer from 3 to 6.

* * * * *